United States Patent [19]

Singleton

[11] 4,061,546

[45] Dec. 6, 1977

[54] PURIFICATION OF ACETIC ACID

[75] Inventor: Thomas C. Singleton, Texas City, Tex.

[73] Assignee: Monsanto Company, St. Louis, Mo.

[21] Appl. No.: 671,233

[22] Filed: Mar. 29, 1976

[51] Int. Cl.$^2$ .............................................. B01D 3/34
[52] U.S. Cl. ..................................... 203/31; 203/33; 203/41; 203/51; 203/53; 203/61; 204/97; 260/541
[58] Field of Search ....................... 203/31, 29, 34, 35, 203/41, 39, 28, 33, 32, 16, 50, 51, 53, 61; 260/541; 204/97

[56] References Cited

U.S. PATENT DOCUMENTS

| 2,149,765 | 3/1939 | Goos et al. | 203/31 |
| 2,255,421 | 9/1941 | Groll et al. | 203/31 |
| 2,278,831 | 4/1942 | Cockerille | 203/31 |
| 3,439,026 | 4/1969 | Patton et al. | 260/540 |

Primary Examiner—Wilbur L. Bascomb, Jr.
Attorney, Agent, or Firm—Elizabeth F. Sporar

[57] ABSTRACT

Formic acid is removed from acetic acid substantially free of halide impurities but containing small amounts of formic acid by contacting the acid with a compound of hexavalent chromium and recovering the purified acid from the resulting mixture by distillation, ion-exchange, or the like. In a preferred embodiment, the acid to be purified is distilled in the presence of a solution of the hexavalent chromium compound, the purified acid being obtained as the overhead product while the bottoms stream contains the reduced chromium compound. With the preferred chromium trioxide as treating agent, this compound can be recovered for re-use by adding a strong mineral acid to the bottoms stream from the distillation, electrolytically oxidizing the chromium compound contained therein, and separating chromium trioxide from the strong mineral acid solution.

6 Claims, 1 Drawing Figure

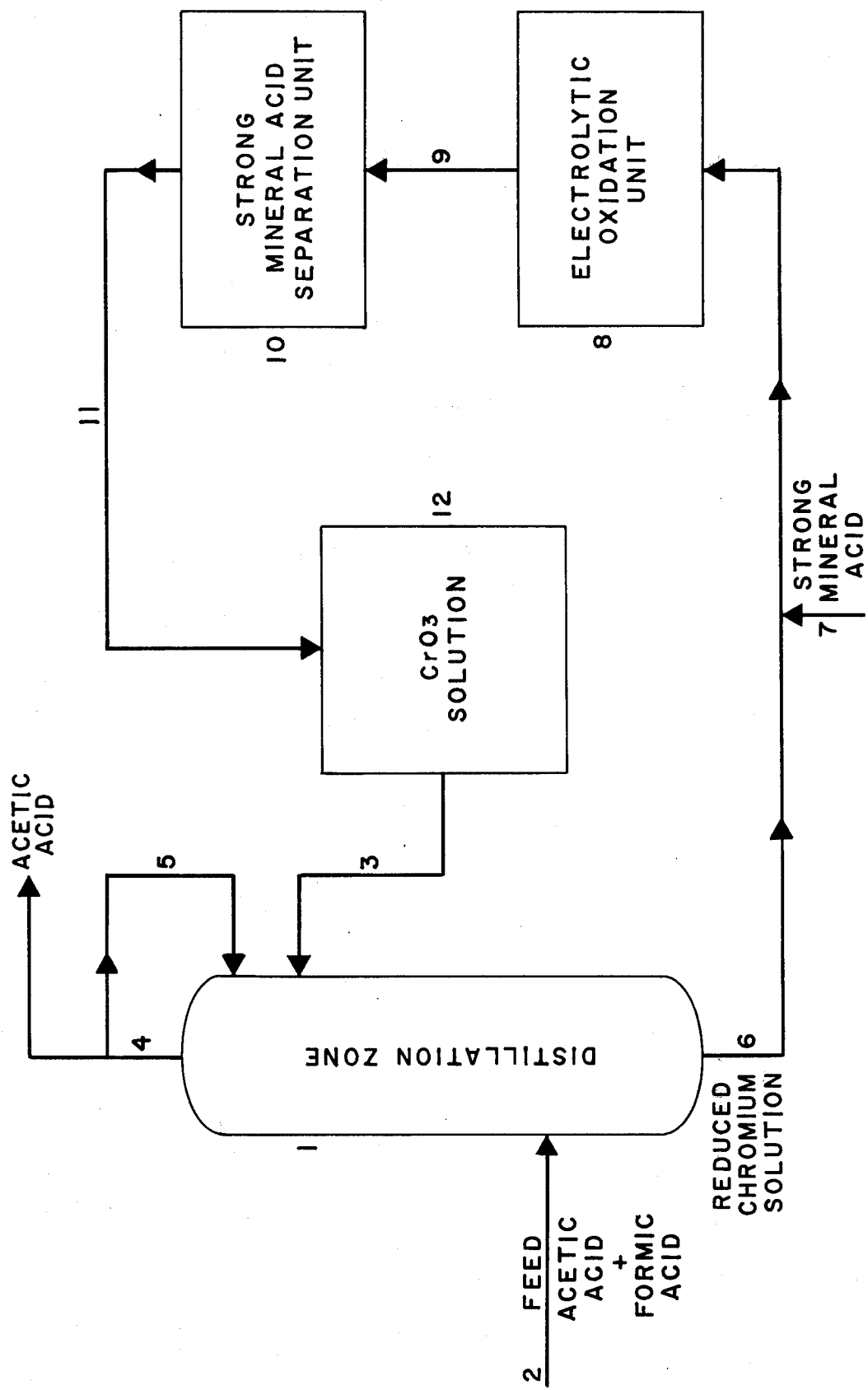

PURIFICATION OF ACETIC ACID

BACKGROUND OF THE INVENTION

The present invention relates to removal of minor amounts of formic acid from acetic acid.

Acetic acid, one of the more important acids of commerce, is produced commercially in large quantities by the liquid phase oxidation of low-molecular-weight hydrocarbons such as butane and by the carbonylation of methanol or an ester, ether or halide derivative thereof, using a catalyst system formed on mixing of a rhodium or iridium compound and a halogen component such as hydrogen iodide or methyl iodide. The acetic acid produced by these processes is of high quality but it sometimes contains small amounts of formic acid. Certain commercial specifications require that the formic acid content in acetic acid should desirably be less than 500 ppm, i.e., 500 parts per million parts of acetic acid, but in some instances the acceptable limit for formic acid is specified as <100 ppm.

Many techniques have been used to decrease the formic acid contained in acetic acid. For example, acetic acid containing this contaminant has been treated according to U.S. Pat. No. 2,656,379 by passing it over activated alumina at temperatures above 260° C to decompose the formic acid therein. However, at the elevated temperature involved in the use of this and certain other dehydrogenation catalysts disclosed in Russian Pat. No 57,862, substantial decomposition of the acetic acid also occurs. Selective oxidation both with and without added oxygen or air has been effected using a variety of catalysts such as platinum, osmium, iridium, palladium, ruthenium and rhodium supported on activated carbon or aluminum oxide and metal molybdates as described, for example, in U.S. Pat. Nos. 2,688,635, 2,913,492, 2,900,413, 3,196,176, 3,384,659 and 3,560,560. Other processes for selectively decomposing formic acid in mixtures containing formic acid and acetic acid have been developed which employ complex compounds of a noble metal of Group VIII such a platinum, osmium, rhodium or preferably ruthenium or iridium, these compounds being refluxed with the acid mixture as described in U.S. Pat. No. 3,488,383. In another method described in U.S. Pat. No. 3,459,707, the acid mixture is contacted in the liquid phase at temperatures from about 80° to 140° C with molecular oxygen in the presence of a catalyst comprising a soluble compound of a platinum group metal and a redox system and preferably also in the presence of a base. While such processes are effective, they are neither as simple nor as economical to operate as might be desired, particularly when only trace amounts of formic acid are present in the acetic acid to be treated. It is, accordingly, an object of the present invention to provide a relatively simple method for removing small amounts of formic acid from acetic acid which is readily adaptable for use in conjunction with the usual distillation techniques for purification of acetic acid.

SUMMARY

According to the invention, acetic acid substantially free of halide impurities but containing minor amounts of formic acid is intimately contacted with a compound of hexavalent chromium and the acid containing less than 100 ppm formic acid is recovered from the mixture. In a preferred embodiment of the invention, acetic acid substantially free of halide impurities but containing minor amounts of formic acid is distilled in the presence of a solution of a compound of hexavalent chromium, acetic acid having a formic acid content less than 100 ppm is withdrawn as an overhead product and a bottoms product is withdrawn containing acetic acid and the chromium compared containing chromium in its reduced form ($Cr^{+3}$). The bottoms stream may be disposed of or, in accord with a more preferred embodiment of the invention wherein $CrO_3$ is the treating agent, may be treated to recover the chromium values for re-use to preclude any environmental problems which might arise relating to disposal of the metal-containing stream. To effect chromium recovery, a strong mineral acid is added to the bottoms stream, the resulting solution is charged to an electrolytic cell, a direct electric current is passed through said cell whereby the chromic acetate is oxidized to chromium trioxide, and the chromium trioxide is then separated from the strong mineral acid solution.

DESCRIPTION OF THE PREFERRED EMBODIMENTS

In its simplest aspect, the process of the invention involves contacting of the acetic acid to be purified of formic acid with the hexavalent chromium compound and recovering the purified acid from the resulting treated acid mixture. The contacting can be effected in any manner which provides for good mixing of the hexavalent chromium compound and the acid being treated. Thus, simple stirring in a suitable vessel, circulation of the materials, co-current, counter current or cross-current contacting, boiling, refluxing, and the like, may be used. Generally, the contacting is carried out at a temperature from about 16° to about 200° C, and preferably from about 20° C to about 160° C. Pressure in the contacting operation is not critical and may be atmospheric, subatmospheric or superatmospheric. Preferably, pressure in the contacting step varies from atmospheric to 5 kg/cm². The contact time employed may vary from a few seconds to several hours and up to as much as 10 hours. For practical purposes, however, the contacting time will generally be in the range from about 10 seconds to about 10 minutes.

Compounds containing chromium which are suitable for selectively oxidizing the formic acid impurity by contacting as disclosed above are those containing hexavalent chromium. Examples of the most useful compounds are chromium trioxide and the alkali metal chromates such as sodium chromate, sodium dichromate, potassium chromate, potassium dichromate and the like. Generally, the amount of the chromium compound used is that which is at least equivalent to the stoichiometric amount required to oxidize the formic acid present. Preferably, an amount two to three times that equivalent to the stoichiometric amount is used. Larger excesses can be used if desired but they are actually uneconomical and represent no advantage especially in view of the fact that some method for disposal of the chromium-containing waste left after recovery of the purified acid is usually required.

Recovery of the acid stream from the treated acid mixture can be carried out by distillation or by ion-exchange techniques and can be on a batch-wise or continuous basis. The distillation may be carried out in a distillation system of practically any efficiency. Simple flash distillation is effective and it is generally not necessary to employ a column with more than a five theoretical late efficiency. The distillation column may in many instances be an open tubular column of no more than two theoretical plate efficiency or it may be one containing sieve trays, bubble caps, a series of baffles or packing. It is operated in a manner such as to vaporize the acetic acid overhead leaving as a bottoms product heavy ends and other heavy waste materials. Conditions of temperature and pressure for conducting such a distillation are well within the ability of those skilled in the art based on the teachings herein.

An alternate method for recovery of purified acid is to contact the treated acid mixture with a cation exchange resin of the strong-acid or weak-acid type whereby the chromium and/or sodium or potassium when these salts are used is/are adsorbed on the resin. The resin used for removal of chromium is employed in the hydrogen form. Both types are readily available as commercial products. The weak-acid cation exchange resins are mostly copolymers of acrylic or methacrylic acids or esters or the corresponding nitriles but a few of those marketed are phenolic resins. Strong-acid cation exchange resins which are the resins preferred for use in the present invention are constituted predominantly of sulfonated styrene-divinylbenzene copolymers although some of the available resins of this type are phenolformaldehyde condensation polymers. Either the gel or the macroreticular type resin is suitable but the latter is preferred since organic components are present in the stream being treated.

Contacting of the treated acid mixture and the resin can be effected in a stirred vessel wherein the resin is slurried with the mixture with good agitation and the purified acid is then recovered by decantation, filtration, centrifuging, etc. However, recovery of the purified acid will usually be effected by passing it through a fixed-bed column of the resin. The chromium removal step can be carried out as a batch, semi-continuous or as a continuous operation as described above either with manual or automatic control, employing methods and techniques well known in the art of ion-exchange.

The ion-exchange treatment can be effected at temperatures in the range from about 16° to about 120° C, although lower or higher temperatures limited only by the stability of the resin can be employed. Preferred temperatures are those in the range from about 20° to about 90° C. If temperatures above the boiling point of the chromium-containing acid bottoms stream are employed, then operation under pressure will be required to maintain the solution in the liquid phase. However, pressure is not a critical variable. Generally, atmospheric pressure or a pressure slightly above atmospheric is employed but superatmospheric or subatmospheric pressures can be used if desired.

The rate of flow of the treated acid mixture through the resin will, in general, be that recommended by the resin manufacturer and will usually be from about 1 to about 20 bed volumes per hour. After contacting, washing or rinsing of the resin bed with water, with pure acetic acid or with mixtures of pure acetic acid and water is essential for removing all the chromium from the resin bed. The rinsing or washing is effected at the same flow rates as the ion-exchange step.

After it has become exhausted, i.e., when the chromium is breaking through into the effluent, the resin can be regenerated by passing through it a solution of a mineral acid such as sulfuric, hydrochloric, phosphoric and the like. Generally, the acid used in this cycle has a concentration in the range from about 10% to about 50%. Quantities of regenerant and acid employed and procedures are those well established in the art and recommended by the resin manufacturers.

The ion-exchange operation can be cyclic. As the resin becomes exhausted in one bed, the treated acid mixture can be diverted to a fresh bed while the exhausted bed is subjected to regeneration. Also, if desired, the chromium-containing effluent arising from regeneration of the resin bed can be regenerated by electrolytic oxidation techniques to render it suitable for re-use in the contacting step.

A highly suitable method for practicing the process of the invention involves a single distillation zone or column wherein acetic acid substantially free of halide impurities but containing a minor amount of formic acid is distilled in the presence of a solution of a hexavalent chromium compound. The acid to be purified is introduced into the intermediate section of the distillation zone while the solution of chromium compound is introduced into the upper part of the zone. A stream of acetic acid containing less than 100 ppm formic acid is removed overhead from the distillation zone and a stream of acetic acid containing in solution the compound of chromium in its reduced state (+3 valence) is withdrawn from the bottom of the distillation zone.

The distillation zone will generally comprise any type distillation column normally employed for the separation and purification of fluids. It can be of either the packed or plate type or a combination of the packed- and plate-type. Generally, it will comprise a plate-type column having from 2 to 30 and preferably 5 to 25 trays and in an especially preferred embodiment sieve trays will be used although other type trays such as bubble-cap and ballast may be employed.

While the point of introduction of the feed stream to the column can be at any point in the middle third of the column, the feed stream is usually introduced below the mid-point of the column and preferably at or near the bottom of the middle third of the column. The chromium-containing solution can be introduced on any tray above the feed tray in the distillation column but usually this treating agent is added into the upper one-third of the column and more particularly, into the upper one-tenth of the column. Another convenient way of adding the chromium-containing treating agent is to add it to the reflux to the column. The chromium compound is introduced into the column in solution form and preferably in solution in acetic acid although aqueous solutions and solutions in which mixtures of acetic acid and water serve as solvents can be employed.

The temperatures and pressures employed in the distillation column may vary considerably. As a practical matter, the column will most often be operated at pressures from atmospheric up to about 5 kg/cm² although subatmospheric pressures may be employed if desired as well as superatmospheric pressures well in excess of 8 kg/cm². Preferably, however, in this purification of acetic acid, column pressure will usually be maintained within the range of 0 to 3 kg/cm².

Temperatures in the column will normally be between the boiling point of the acetic acid being purified at the pressure of the column and the temperature at which a satisfactory boil-up rate is achieved at such pressue. At the preferred pressures, the bottoms temperature will generally be within the range of from approximately the boiling point of the acid at the pressure employed to as high as 200° C and higher. Preferably, however, these bottoms temperatures are maintained below about 160° C. Overhead temperatures are at the boiling point of the acid at the pressure of the column.

The process of the invention is particularly adaptable for treating acetic acid produced by carbonylation of methanol using catalyst systems consisting of a rhodium or iridium compound and a halogen component which is bromine, iodine an iodide or a bromide as described and claimed in U.S. Pat. Nos. 3,772,380 and 3,769,329. In order to recover a pure acetic acid from the reaction mixture from such processes, the mixture is subjected to an adiabatic flash for separation of the catalyst as the liquid phase for recycle purposes and the vapor-phase mixture including the carbonylation products is then distilled in a multiple-column distillation train. In the first column, low-boiling components are removed, in a second, water is removed to dry the acid, and in a third column, the so-called product column, higher boiling components are separated and halide impurities are removed. Halide impurities can be removed as described and claimed in U.S. Pat. No. 3,709,795 using inorganic oxidizing agents but preferably they are eliminated by a two-column distillation in the presence of an alkali metal compound such as potassium hydroxide as described in U.S. Pat. No. 3,772,156. The product free of halide impurities, but still containing small amounts of formic acid can then be subjected to further distillation in the presence of a hexavalent chromium compound as described herein to obtain acetic acid containing less than 100 ppm formic acid.

In a more preferred embodiment of the present invention, chromium trioxide is employed as the treating agent in a distillation column and regeneration of the chromium$^{+3}$ in the bottoms stream is effected by electrolytic oxidation. As mentioned previously, this precludes any disposal problems related to handling of the bottoms stream from the formic acid removal column and makes the chromium available for re-use and recycle of the process.

Such a process can be more fully explained by reference to the accompanying drawing which is a schemtic flow diagram thereof. In the interest of simplicity, valves, pumps, condensers, accessory equipment and constructional details of equipment are omitted.

Referring now to the drawing, a stream of acetic acid containing a small amount of formic acid, such as e.g., about 400 ppm, is fed via line 2 to the distillation column 1 wherein it is distilled in contact with a solution of chromium trioxide in acetic acid introduced into the upper section of the column 1 through line 3 coming from the CrO$_3$ solution reservoir 12. An overhead stream of acetic acid containing less than 100 ppm formic acid is removed via line 4 and sent to purified acetic acid product storage. A portion of the overhead stream 4 is removed via line 5, condensed and returned to the column 1 as reflux.

A stream of acetic acid containing in solution the compound of chromium in its reduced state ($+3$ valence) is removed from the bottom of the distillation column 1 through line 6. A strong mineral acid such as phosphoric or sulfuric is added through line 7 to stream 6 and the resulting mixture is introduced into an electrolytic oxidation unit or cell 8 as the electrolyte to both the anolyte and catholyte reservoirs of the unit or cell and is circulated through the anode and cathode compartments. Samples of the anolyte are withdrawn periodically from the electrolytic cell 8 via line 9 and introduced into separation unit 10 where the strong acid introduced via line 7 is separated from the chromium trioxide by conventional means, e.g., by an ion exchange technique wherein the anolyte is passed through an anion exchanger to remove the chromium$^{+6}$ ions, these ions are then displaced from the resin by elution with another anion, preferably an acid such as HCl, H$_3$PO$_4$ and the like. The eluent is collected, concentrated and the chromium trioxide is recovered therefrom by crystallization. The recovered oxide is dissolved in acetic acid and fed by means of line 11 into the chromium trioxide solution reservoir 12.

The electrolytic oxidation is conducted in a suitable cell system having a diaphragm separating the anolyte from the catholyte. The size, shape and dimensions of the electrolytic cell as well as the materials from which it is fabricated are not critical. Since a strong mineral acid is used in the cell, it is preferable that the surfaces of the cell exposed to the mineral acid be resistant to attack by the acid in order to obtain longer cell life and minimize maintenance requirements. A cell with both a lead cathode and a lead anode is satisfactory. A carbon cathode is also acceptable as well as a platinum-plated steel cathode.

Prior to charging to the electrolytic cell, a strong mineral acid is added to the bottoms stream containing the Cr$^{+3}$ compound. Preferred strong mineral acids are sulfuric acid and phosphoric acid with sulfuric acid preferred. The acid concentration is not critical so long as the chromium remains in solution during the course of the electrolytic oxidation process. Acid concentrations of about 40 to 60% are conveniently used. Higher acid concentrations provide high electrical conductivity and minimize the amount of water to be removed in the recovery of the chromic acid from the anolyte. The acid must not be so concentrated as to cause precipitation of chromic acid in the electrolytic cell.

The current density of the cell is likewise not critical to the chemistry of the process. A high current density is desirable for economic reasons. In general, current densities from 20 to 40 amps/square decimeter are employed and current densities over 40 amps/square decimeter are achievable. The amount of anode surface area required for a fixed electrolytic capacity is inversely proportional to the current density.

High current densities are achieved by promotion of turbulent flow across the surface of the anode. A highly efficient cell employing turbulent flow across the anode will oxidize a greater volume of ions than a normal cell. This means that for a given volume of ions to be oxidized fewer higher efficiency cells are required than normal cells. This reduces not only the initial capital investment in the electrolytic cells but also minimizes the plant space required as well as the inventory of the chromium and the acid.

Turbulent flow may be achieved by high velocity flow and close electrode spacing. Maximum flow velocity is limited only by the structural strength of cell components and pumping capacity. Electrode spacing will depend on the size, type and configuration of the cell components. In suitable cells the anode may be spaced less than one-fourth inch from the cathode. In other cells achieving current densities of 40 amperes per square decimeter of anode surface area or more the spacing may be greater than one-half inch. Neither the spacing nor the flow rate of itself is critical. The key consideration is to maintain turbulent flow across the surface of the anode and minimize stagnation of $+6$ chromium ions at the anodic surface.

Another key factor in achieving high efficiency in cell operation is minimizing the flow of +6 chromium ions to the cathode where they would be reduced to a lower oxidation state. This can be achieved by a number of procedures. The cell may be designed so that the direction of high velocity flow is always away from the cathode and toward the anode. A porous anode and cathode may be useful in such designs. Another method of preventing the +6 chromium ions from migrating to the cathode is to erect a barrier the anode and cathode. Such a barrier can be a porous charged conductive shield to repel the ions as they try to approach the cathode. A more effective barrier is the use of a porous membrane to separate the anolyte from the catholyte. The porous membrane separates the electrolytic cell into two compartments, one of which compartments contains the anode and the second of which contains the cathode. If the cell contents, the electrolyte, is to pass from one compartment to the other, it must pass through the porous membrane. The membrane is a more effective barrier where the catholyte is maintained at a higher pressure than the anolyte. Such a pressure differential may be easily maintained by charging the chromic oxide to the compartment containing the cathode and withdrawing the chromium trioxide solution from the compartment containing the anode at about equivalent rates. In this manner, any flow through the membrane is directed away from the cathode and toward the anode. One of several satisfactory porous membranes, which are resistant to a strongly acid environment, is a cloth of polytetrafluoroethylene.

In starting up the continuous regeneration, the acid bottoms to which a strong acid has been added is charged as electrolyte to both the anolyte and catholyte reservoirs of the electrolytic cell. This electrolyte at a temperature of about 50° to 60° C is circulated through the anode and cathode compartments at a rate of approximately 6 feet/second. When the flows are balanced a potential of about 4 volts is applied. Current density is from about 20 to about 40 amps/square decimeter. Samples of the anolyte are withdrawn periodically to follow conversion of chromium$^{+3}$ to chromium$^{+6}$ as determined by standard iodometric titration using sodium thiosulfate. When the conversion reaches a predetermined level, anolyte is continuously withdrawn from the system. Fresh acid bottoms containing strong acid functioning as the electrolyte is added to the circulating anolyte at the same rate that anolyte is being withdrawn. The rate of addition of and withdrawal is such that a predetermined conversion is obtained. The anolyte is then treated to separate the chromium trioxide from the strong acid,

EXAMPLE 1

Several samples of acetic acid containing 273 ppm of formic acid were treated as described below. The acetic acid had been prepared by subjecting the reaction mixture from the carbonylation of methanol in contact with a catalytic system formed on mixing of a rhodium compound and methyl iodide in the presence of CO to an adiabatic flash and distilling the vaporized carbonylation product in a first column to remove an overhead stream containing products boiling lower than acetic acid (a major proportion of water and methyl iodide), a bottoms stream substantially containing all the hydrogen iodide present, and a side stream from the middle portion thereof which is introduced into a second column where all remaining water is removed overhead and a substantially dry acid stream is removed from the bottom of said column, this bottoms stream being introduced into a distillation system such as is described in U.S. Pat. No. 3,772,156 for removal of higher boiling impurities and minor amounts of iodine either as I$^-$, free iodine or methyl iodide by distillation in the presence of potassium hydroxide to recover an acetic acid stream essentially free of all iodine.

The acid was charged to a 200-ml. flask and heated to boiling. A solution of a hexavalent chromium compound dissolved in acetic acid was injected into the flask and the resulting mixture was boiled for an additional thirty seconds. The flask was cooled rapidly and the solution contained therein was analyzed for formic acid content by standard gas chromatographic techniques. Amounts of acid and additive or treating agent employed together with the results obtained are presented in Table 1 below.

TABLE 1

| Sample | Acetic Acid Charged (ml) | Chromium Cmpd. Charged | Chromium Solution (ml) | Chromium Cmpd. Wt. (g.) | Formic Acid in Product (ppm) |
|---|---|---|---|---|---|
| 1 | 100 | CrO$_3$ | 2$^1$ | 0.04 | 80 |
| 2 | 50 | " | 2$^1$ | " | <40 |
| 3 | 75 | " | 2$^1$ | " | <40 |
| 4 | 50 | Na$_2$Cr$_2$O$_7$ | 2$^1$ | 0.0524 | 68 |
| 5 | 50 | " | 3$^2$ | 0.0785 | 44 |

$^1$Contained 0.2 ml H$_2$O total
$^2$Contained 0.3 ml H$_2$O total

EXAMPLE 2

Samples of acetic acid from the same source as that described in Example 1 substantially free of halides but containing 332 ppm of formic acid were distilled in a two-inch Oldershaw distillation column having 30 trays equipped with a stillpot and provided with two separate inlet lines into the column just above the 12th and 24th trays from the bottom, respectively. The acid was introduced on the 12th tray from the bottom at a feed rate of 28 cc/minute. The overhead temperature of the column was maintained at about 118° C and the bottoms temperature at approximately 120° C with the column at substantially atmospheric pressure. The total overhead vapor was withdrawn and condensed, a portion thereof being recovered as product and a second portion being returned to the column as reflux via the inlet above the 24th tray from the bottom at a rate of 34cc/min. A bottoms stream was removed at a rate of 1.5cc/min and discarded. In each run, an aqueous solution of hexavalent chromium compound was introduced into the column via the reflux stream and distillation was continued. The recovered portion of the condensed overhead distillate was analyzed for formic acid content by standard gas chromatographic techniques. The amounts and kind of chromium compound added and the results of the analyses of the distillate are presented in Table 2 below. Concentration of the additive is given relative to the feed rate of the acid to the column.

TABLE 2

| Additive | Additive Conc. (ppm) | Formic Acid Content of Distillate, (ppm) |
|---|---|---|
| None | — | 251 |
| CrO$_3$ | 299 | 119 |
| " | 449 | 80 |
| " | 598 | 45 |
| None | | 232 |
| K$_2$Cr$_2$O$_7$ | 441 | 119 |
| " | 871 | <40 |
| " | 1760 | <40 |

TABLE 2-continued

| Additive | Additive Conc. (ppm) | Formic Acid Content of Distillate, (ppm) |
|---|---|---|
| None | | 312 |
| $Na_2Cr_2O_7$ | 1564 | <40 |

Wht is claimed is:

1. The method for removing formic acid from acetic acid which consists essentially of introducing acetic acid substantially free of halide impurities but containing a minor amount of formic acid into a distillation zone below the midpoint thereof, introducing a compound of hexavalent chromium dissolved in a solvent selected from the group consisting of acetic acid, water and mixtures of acetic acid and water into the upper one-third of said distillation zone, the bottoms temperature of said column being maintained below about 160° C, removing overhead from said distillation zone an acetic acid stream containing less than 100 ppm of formic acid and removing from the bottom of said distillation zone a stream comprising acetic acid and the compound of chromium in its reduced state.

2. The method of claim 1 wherein the amount of said compound of hexavalent chromium is at least equivalent to the stoichiometric amount required to oxidize the formic acid present in said acetic acid.

3. The method of claim 2 wherein said compound of hexavalent chromium is chromium trioxide.

4. The method of claim 2 wherein said compound of hexavalent chromium is potassium dichromate.

5. The method of claim 2 wherein said compound of hexavalent chromium is sodium dichromate.

6. The method of claim 3 wherein said bottom stream from said distillation zone is treated by adding thereto a strong mineral acid, subjecting the resulting strong mineral acid solution to the action of a direct electric current whereby the chromium compound present in its reduced state is oxidized to chromium trioxide and separating the chromium trioxide from the strong mineral acid solution.

* * * * *